(12) United States Patent
Dong et al.

(10) Patent No.: US 9,156,696 B2
(45) Date of Patent: Oct. 13, 2015

(54) PROCESS AND METHOD FOR THE EFFICIENT PREPARATION OF FULLERYNES

(75) Inventors: Xuehui Dong, Akron, OH (US); Wenbin Zhang, Akron, OH (US); Stephen Z. D. Cheng, Akron, OH (US); Roderic P. Quirk, Akron, OH (US)

(73) Assignee: The University of Akron, Akron, OH (US)

( * ) Notice: Subject to any disclaimer, the term of this patent is extended or adjusted under 35 U.S.C. 154(b) by 354 days.

(21) Appl. No.: 13/808,406

(22) PCT Filed: Jul. 6, 2011

(86) PCT No.: PCT/US2011/001182
§ 371 (c)(1),
(2), (4) Date: Feb. 18, 2013

(87) PCT Pub. No.: WO2012/005762
PCT Pub. Date: Jan. 12, 2012

(65) Prior Publication Data
US 2013/0144083 A1    Jun. 6, 2013

Related U.S. Application Data

(60) Provisional application No. 61/362,128, filed on Jul. 7, 2010.

(51) Int. Cl.
| | |
|---|---|
| C07C 69/52 | (2006.01) |
| C01B 31/02 | (2006.01) |
| C07C 17/16 | (2006.01) |
| C07C 23/18 | (2006.01) |
| C07C 29/42 | (2006.01) |
| C07C 29/68 | (2006.01) |
| C07C 35/44 | (2006.01) |
| C07C 69/606 | (2006.01) |
| C07C 69/63 | (2006.01) |

(52) U.S. Cl.
CPC ............ *C01B 31/0213* (2013.01); *C07C 17/16* (2013.01); *C07C 23/18* (2013.01); *C07C 29/42* (2013.01); *C07C 29/68* (2013.01); *C07C 35/44* (2013.01); *C07C 69/606* (2013.01); *C07C 69/63* (2013.01); *C07C 2104/00* (2013.01)

(58) Field of Classification Search
CPC .................................................. C01B 31/0213
See application file for complete search history.

(56) References Cited

U.S. PATENT DOCUMENTS

| 6,380,434 B1 | 4/2002 | Chiang |
| 7,018,599 B2 | 3/2006 | Nakamura et al. |
| 7,671,230 B2 | 3/2010 | Bolskar et al. |
| 2004/0062971 A1 | 4/2004 | Nuber |
| 2005/0239717 A1 | 10/2005 | Kronholm et al. |
| 2008/0213324 A1 | 9/2008 | Zhou et al. |
| 2008/0221240 A1 | 9/2008 | Swager et al. |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Thilgen et al, Chemical Reviews, Structural Aspects of Fullerene Chemistry—A Journey through Fullerene Chirality, 2006 106, pp. 5049-5135.*
Zhang et al, Macromolecules, "Clicking" Fullerene with Polymers: Synthesis of [60]Fullerene End-Capped Polystyrene, 2008, 41, pp. 515-517.*

* cited by examiner

*Primary Examiner* — Paul A Zucker
(74) *Attorney, Agent, or Firm* — Renner Kenner Greive Bobak Taylor & Weber

(57) ABSTRACT

The preparation of novel fullerynes which are fullerenes (e.g. $C_{60}$, $C_{70}$, $C_{80}$, etc.) that contain one or more alkyne functionalities and may contain additional functional groups such as hydroxyls, halogens, esters, haloesters, phenyl, oligo(ethylene glycol)s, perfluorinated alkyl chains, and the like. Two desired preparation routes are disclosed. The first one is the Fischer esterification in desired solvents using a special designed reactor in contrast to the heretofore initial Steglich reaction that results in side reactions and low yields. The second one uses acetylide Grignard reagents that have reduced nucleophilicity and higher stability in contrast to the use of heretofore initial lithium organyls or other Grignard reagents that would add to $C_{60}$ with possible multi-additions in an uncontrollable manner.

10 Claims, 1 Drawing Sheet

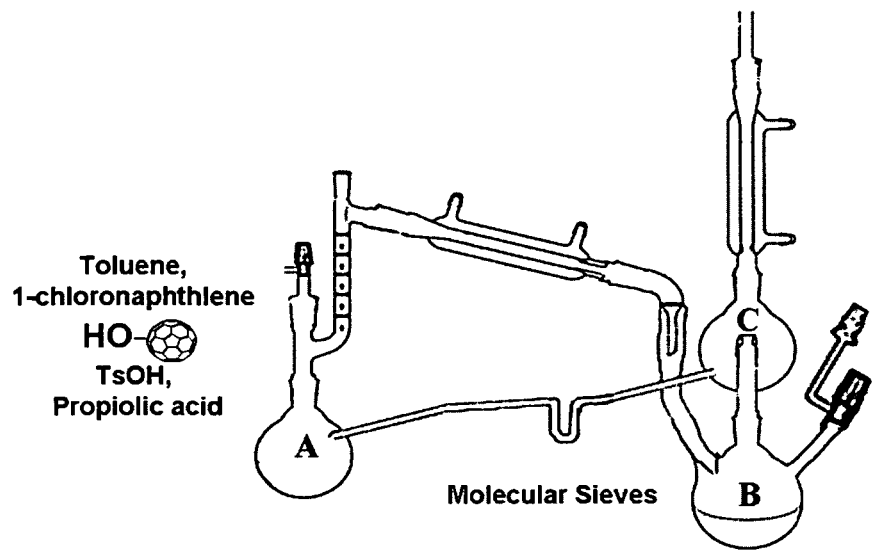

PROCESS AND METHOD FOR THE EFFICIENT PREPARATION OF FULLERYNES

CROSS REFERENCE

This patent application claims the benefit and priority of U.S. provisional application 61/362,128, filed Jul. 7, 2010, for PROCESS AND METHOD FOR THE EFFICIENT PREPARATION OF FULLERYNES, which is hereby fully incorporated by reference.

FIELD OF THE INVENTION

The present invention relates to the preparation of novel fullerynes which are fullerenes (e.g. $C_{60}$, $C_{70}$, $C_{80}$, etc.) that contain one or more alkyne functionalities and may contain additional functional groups such as hydroxyls, halogens, esters, haloesters, phenyl, oligo(ethylene glycol)s, perfluorinated alkyl chains, and the like. More specifically, the present invention relates to two desired preparation routes. The first one is the Fischer esterification in desired solvents using a special designed reactor in contrast to the heretofore initial Steglich reaction that results in side reactions and low yields. The second one uses acetylide Grignard reagents that have reduced nucleophilicity and higher stability in contrast to the use of heretofore initial lithium organyls or other Grignard reagents that would add to $C_{60}$ with possible multi-additions in an uncontrollable manner.

BACKGROUND OF THE INVENTION

Fullerenes are molecular carbon allotropes in the form of a hollow sphere or ellipsoid with different numbers of carbon atoms. The most prevalent fullerene is $C_{60}$, also known as buckyball since it resembles the shape of a soccer ball. Different numbers of carbon atoms are also possible, such as $C_{70}$, $C_{76}$, $C_{84}$. They are all fascinating carbon nanostructures that are not only aesthetically appealing but also have outstanding structural, magnetic, superconducting, electrochemical, and photochemical properties with great potential in both biological applications and material science. However, the poor compatibility of pristine fullerenes with other materials severely limits their derivatization and utilization. Despite the diverse routes to functionalize fullerenes, only a few are highly efficient and specific. This is especially the case for polymers. The often unavoidable multiple-addition and the reactive nature of fullerene to various reaction intermediates always leads to a mixture of unfunctionalized fullerene, homopolymer, mono-, and multi-adducts, which, unlike small molecules, are often difficult to purify. Moreover, the reduced chain end reactivity in polymers (such as azides) sometimes requires drastic reaction conditions (high temperature, long time, etc.), which could lead to potential polymer backbone degradation. Also, some derivatives are unstable either by themselves (eg. retro D-A reaction) or with singlet oxygen generated by fullerene core (eg. azafulleroid). All of these issues can complicate the study of the physics of fullerene polymers. Therefore, it is of great interest to develop a general method for the efficient preparation of fullerene materials.

Heretofore, some fulleryne compounds have been prepared by "Click" reactions which are known to the literature and to the art. An example of such a compound is set forth in Chart 1 and Scheme 1 wherein Fulleryne01 is produced from fullerene $C_{60}$. Fulleryne01 can undergo "click" reactions with azide-functionalized materials as shown in Scheme 1.

Chart 1. Chemical Structure of [60]Fullerene ($C_{60}$) and Fulleryne01.

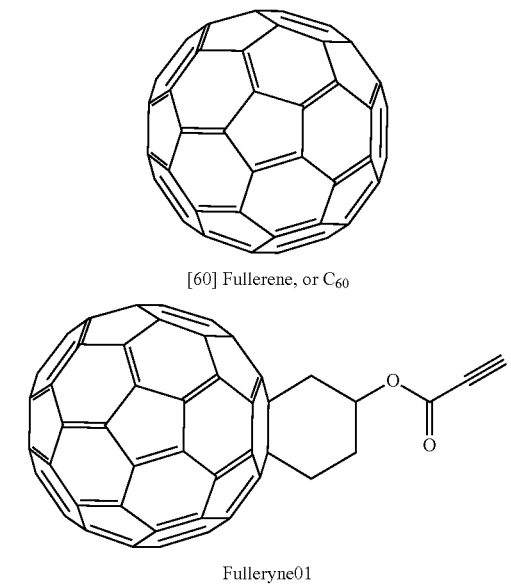

[60] Fullerene, or $C_{60}$

Fulleryne01

Scheme 1. The preparation of Fulleryne01 and its "Click" Reaction with PS-N$_3$ prepared via ATRP[a]

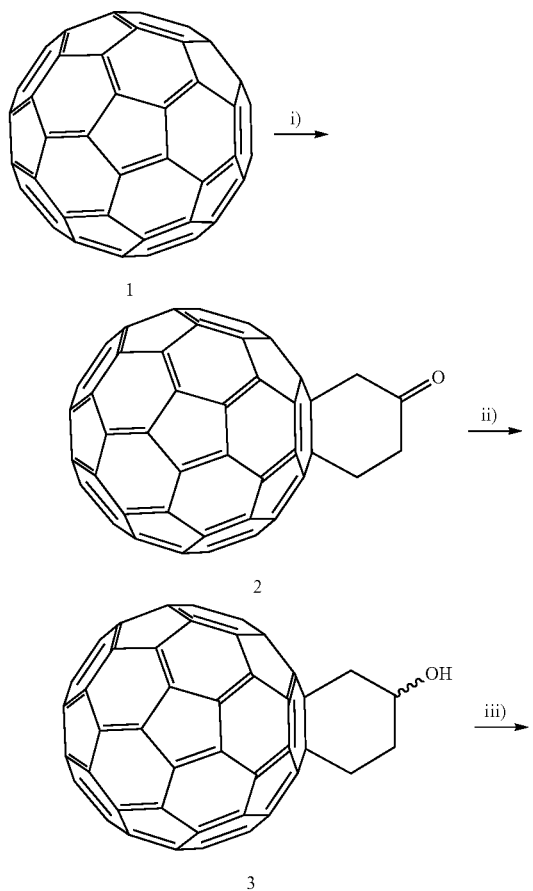

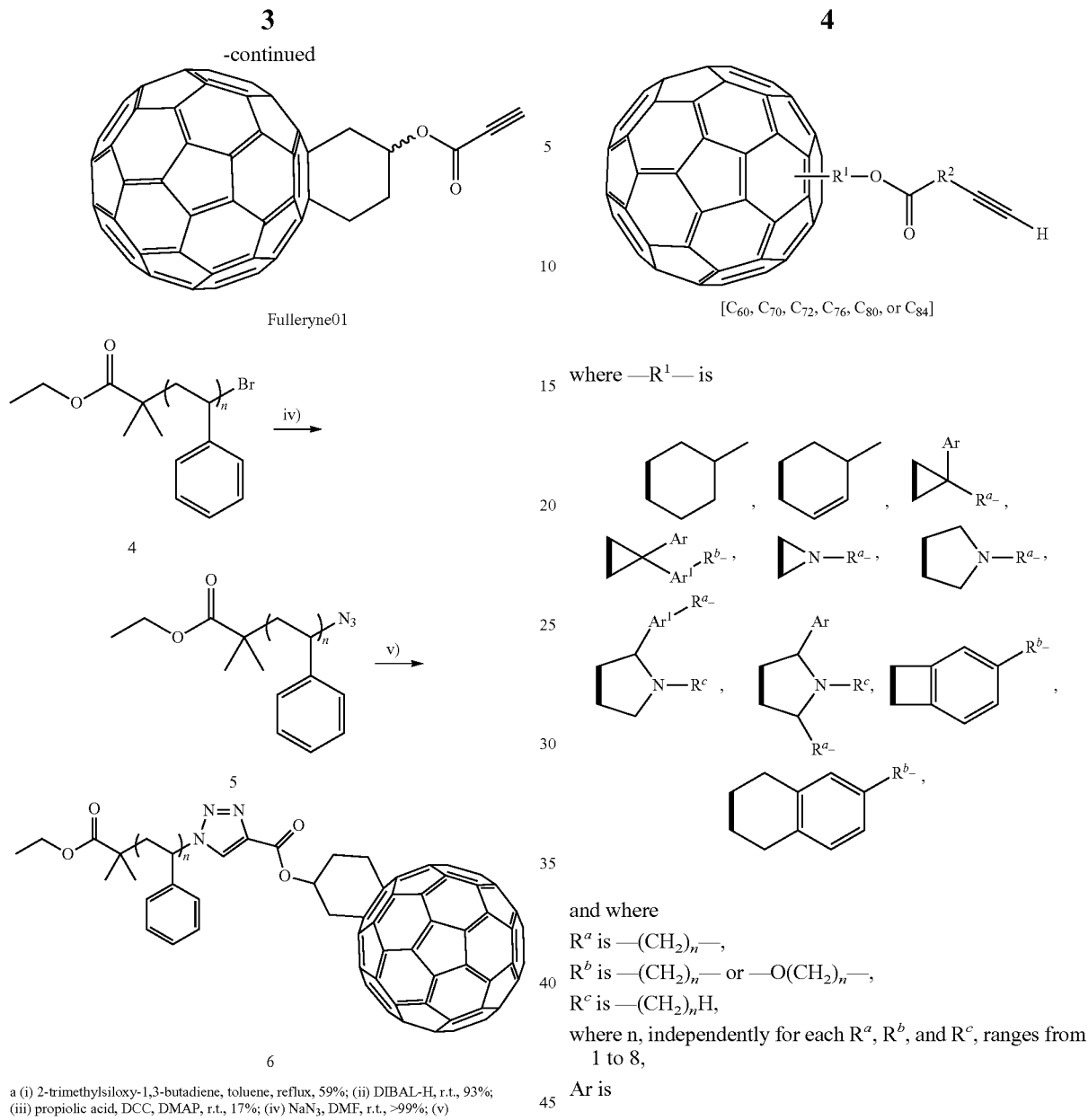

a (i) 2-trimethylsiloxy-1,3-butadiene, toluene, reflux, 59%; (ii) DIBAL-H, r.t., 93%; (iii) propiolic acid, DCC, DMAP, r.t., 17%; (iv) NaN₃, DMF, r.t., >99%; (v) Fulleryne01, CuBr, PMDETA, toluene, r.t., 95%.

As apparent from Scheme 1, while Fulleryne01 can be produced by Steglich esterification, the yield thereof is very low, such as about 17 wt. percent.

SUMMARY OF THE INVENTION

Thus, it is highly desirable to develop a variety of versatile fulleryne compounds that can be facilely prepared, for example Fullerynes02, 03, 04, 05, and 06, and subsequently can be used for the general and efficient development of stable, well-defined fullerene materials under very mild reaction conditions, e.g. Scheme 7 located at the end of the Detailed Description.

A functional fulleryne composition comprises: the formula

[$C_{60}$, $C_{70}$, $C_{72}$, $C_{76}$, $C_{80}$, or $C_{84}$]

where —$R^1$— is and where
$R^a$ is —$(CH_2)_n$—,
$R^b$ is —$(CH_2)_n$— or —$O(CH_2)_n$—,
$R^c$ is —$(CH_2)_n$H,
where n, independently for each $R^a$, $R^b$, and $R^c$, ranges from 1 to 8,
Ar is

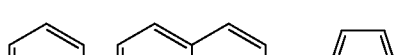

mono-substituted at different positions, and
$Ar^1$ is

di-substituted as indicated, and
wherein $R^2$ is nonexistent or is an alkyl having from 1 to about 6 methylene units; or
wherein said $C_{60}$, $C_{70}$, $C_{72}$, $C_{76}$, $C_{80}$, or $C_{84}$ Fulleryne has an additional

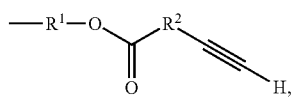

group wherein $R^1$ and $R^2$, independently are the same or different as the above $R^1$ and $R^2$ groups.

A further functionalized Fulleryne composition comprises: the formula

[Fulleryne A

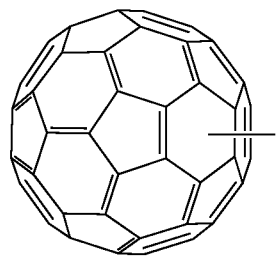

[$C_{60}$, $C_{70}$, $C_{72}$, $C_{76}$, $C_{80}$, or $C_{84}$]

Fulleryne B

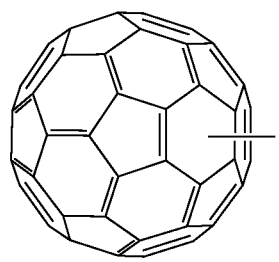

[$C_{60}$, $C_{70}$, $C_{72}$, $C_{76}$, $C_{80}$, or $C_{84}$]

Fulleryne C]

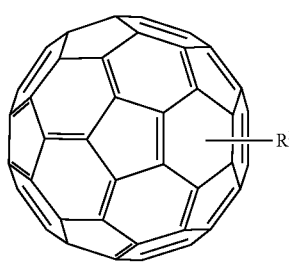

[$C_{60}$, $C_{70}$, $C_{72}$, $C_{76}$, $C_{80}$, or $C_{84}$]

or wherein said Fulleryne A, B, C, respectively has an additional substituted functional group

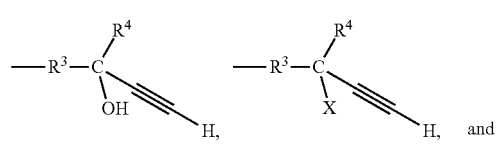

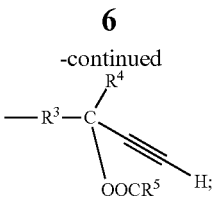

where —$R^3$— is —$CH_2CH_2$—, —CH=CH—

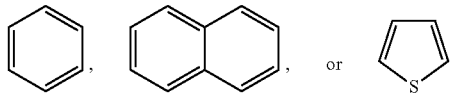

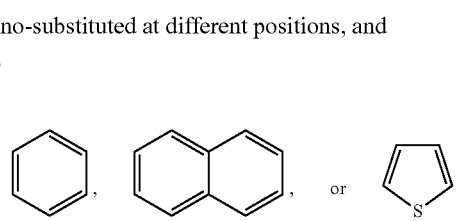

and

—$R^4$— is nonexistent, —$CH_2$—, or —$(CH_2)_nH$ where n ranges from 0 to 8, or hydrogen, and where $R^a$ is —$(CH_2)_n$—, $R^b$ is —$(CH_2)_n$— or —$O(CH_2)_n$—

$R^c$ is —$(CH_2)_nH$, where n, independently for each $R^a$, $R^b$, and $R^c$, ranges from 1 to 8, Ar is (benzene), (naphthalene), or (thiophene)

mono-substituted at different positions, and $Ar^1$ is (benzene), (naphthalene), or (thiophene)

di-substituted as indicated.

where $R^5$ is —$(CH_2)_nH$, or —$(CH_2)_n$—X where n, independently, is from 1 to about 8,

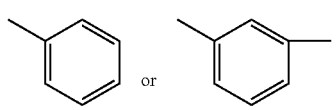

where X is fluoro, chloro, bromo, or iodo.

BRIEF DESCRIPTION OF THE DRAWINGS

FIG. 1 relates to a Reactor Design for the Fischer Esterification of Fullerene Derivatives.

DETAILED DESCRIPTION OF THE INVENTION

In general, the present invention sets forth two processes, i.e. Fisher esterification and Grignard reaction, for the preparation of a variety of fullerynes with high yields. The fullerynes thus obtained have well-defined structure and possess high efficiency with respect to subsequent "click" reactions. They can also be further derivatized to prepare multifunctional materials.

Specific fullerynes can be made by the present invention as set forth in Chart 2. However, as previously noted, many other functional groups can be added other than those specifically set forth within the schemes and examples of the present invention.

Chart 2. Structures of Exemplary Produced Fullerynes of the Present Invention.

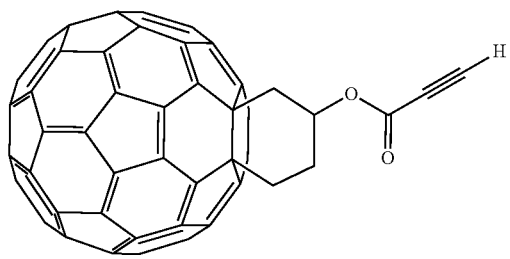

Fulleryne01

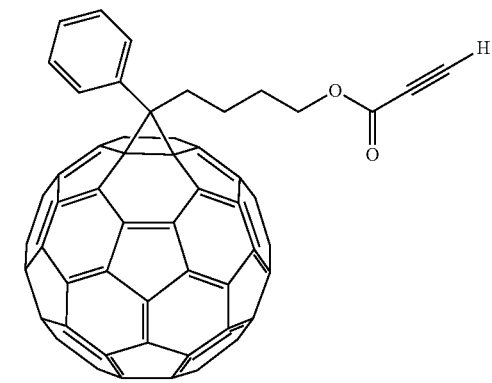

Fulleryne02

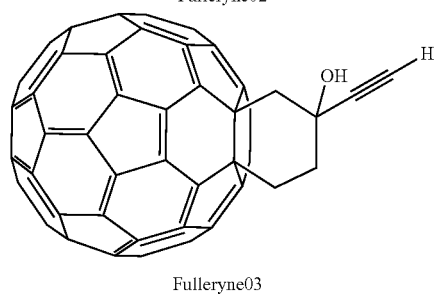

Fulleryne03

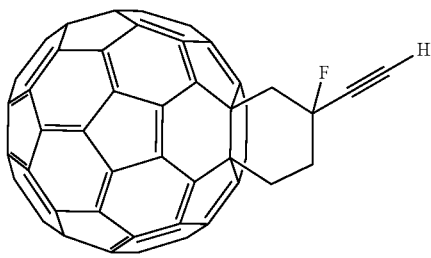

Fulleryne04

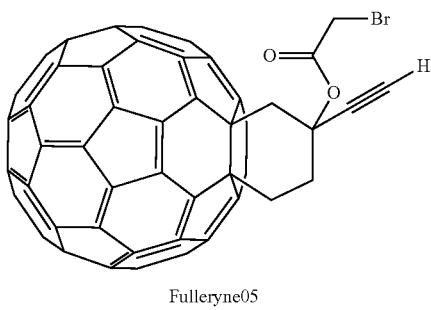

Fulleryne05

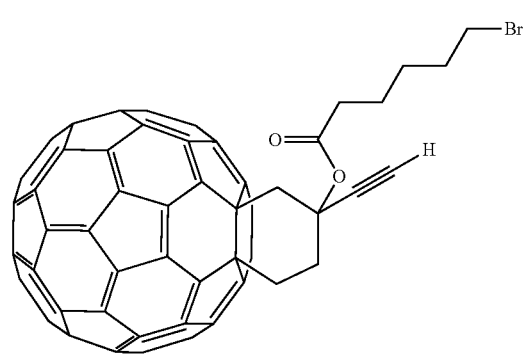

Fulleryne06

According to some of the aspects of the present invention, a method for the production of high yields of fullerenes such as Fulleryne01 and Fulleryne02 comprises reacting a hydroxyl-functionalized fullerene (or named "fullerenol") with alkyne-functionalized carboxylic acids, such as propiolic acid, using Fischer esterification in a specifically designed reactor with desired solvents. The use of selective solvents and reactors allows the equilibrium to be manipulated to proceed substantially to the product side, giving high yield of fullerynes. The generic reaction of the noted Fulleryne01 and Fulleryne02 is set forth in generic Scheme 2.

Scheme 2. Preparation of Fullerynes from Fullerenols by Fischer Esterfication

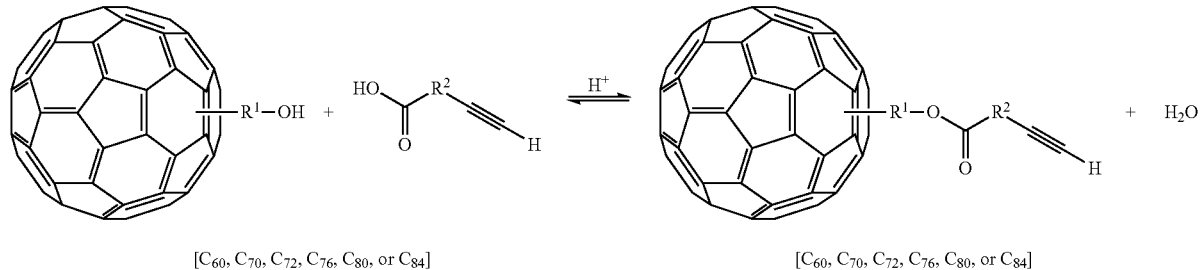

[$C_{60}$, $C_{70}$, $C_{72}$, $C_{76}$, $C_{80}$, or $C_{84}$]     [$C_{60}$, $C_{70}$, $C_{72}$, $C_{76}$, $C_{80}$, or $C_{84}$]

wherein $R^1$ can be a variety of spacers linking fullerene core and the hydroxyl group as shown in Chart 3 and $R^2$ is nonexistent, or an alkyl having from 1 to about 6 methylene units with from 1 to about 3 methylene units being preferred. With respect to the production of Fulleryne01, $R^1$ is a 2-cyclohexyl ring fused to $C_{60}$, $C_{70}$, $C_{72}$, $C_{76}$, $C_{80}$, $C_{84}$ core (—$CH_2CHCH_2CH_2$—) and $R^2$ is nonexistent. With respect to the production of Fulleryne02, $R^1$ is $PhCCH_2CH_2CH_2CH_2$— and $R^2$ is nonexistent.

Chart 3. Various $R^1$ Linking Spacers Between $C_{60}$ $C_{70}$, $C_{72}$, Etc. And Hydroxyl Group are as Follows:

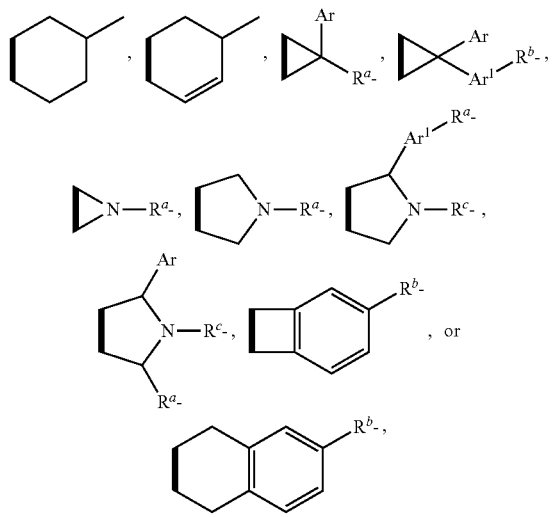

where —$R^1$— is

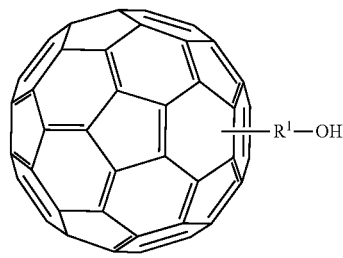

and where
$R^a$ is —$(CH_2)_n^-$,
$R^b$ is —$(CH_2)_n^-$ or —$O(CH_2)_n^-$,
$R^c$ is —$(CH_2)_nH$, where n, independently for each $R^a$, $R^b$, and $R^c$, ranges from 1 to 8,
Ar is

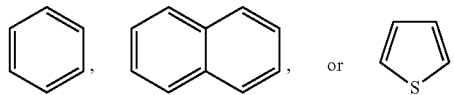

mono-substituted at different positions, and
$Ar^1$ is

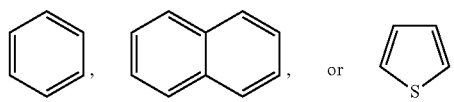

(di-substituted as indicated.

Since π-electron-withdrawing groups such as carbonyl group in Fulleryne01 also promote side reactions, see Scheme 1, it is more preferable to use the σ-electron-withdrawing groups, such as hydroxyl (Fulleryne03) and fluorine (Fulleryne04), to activate the alkyne for the Cu-catalyzed azide acetylene cycloaddition (CUAAC). The existence of a hydroxyl group also allows the installment of other functionalities onto the fulleryne, such as a bromine group (Fulleryne05, Fulleryne06). Fulleryne05 and Fulleryne06 were designed with a highly reactive primary bromo group, which could be readily transformed into other functionalities by highly efficient nucleophilic substitution.

These functional fulleryne compounds of the present invention are produced in relatively high, pure yields and may be coupled to other compounds using "click" reactions to improve their compatibility with other compounds.

To avoid side reactions that might be present in the preparation of fullerynes or in the "click" reaction, it is highly desirable to find reagents and reaction conditions that differentiate the reactivity of the acetylene groups and the $C_{60}$ double bonds to facilitate the synthesis. ($C_{60}$ is utilized as an example throughout the specification but it is to be understood that other Fullerenes can also be used.) The reactivity of double bonds on $C_{60}$ is known to be similar to that of an electron-deficient olefin. Alkynes and olefins are both unsaturated carbon-carbon bonds and susceptible to similar reactions. When chemically modifying $C_{60}$, etc., to attach an acetylene group, it is necessary to consider any associated side reactions. Protection/deprotection scheme is usually used. Alternatively, alkyne group can be installed by reactions that do not involve the double bonds on $C_{60}$, such as esterification or etherification reaction. As noted above, to improve the step economy and the overall process efficiency, two methods have been developed for the preparation of fullerynes.

The first method improves the yield of Fulleryne01. Desirably a reactor is utilized as set forth in FIG. 1. It utilizes three flasks: reaction flask (A), water-removal flask (B), and solvent reservoir (C). The equilibrium reaction takes place in reaction flask (A). The azeotropic distillation removes water from reaction flask (A) to the flask (B), where the moisture is removed and the solvent is redistilled to solvent reservoir (C) and flow back to reaction flask (A) to continue the cycle and push the reaction to completion. It thus forms a unidirectional circulating system from reaction flask (A), to water-removal flask (B), then solvent reservoir (C), and then back to reaction flask (A). The first method modifies the reaction conditions of the Fischer esterification reaction (Scheme 3) and produces increased yield. This is due to the use of desired aromatic solvents, such as 1-chloronaphthalene, 1-methylnaphthalene, 1,2-dichlorobenzene, that have high solubility for fullerene derivatives and a special reactor (FIG. 1) that allows continuous removal of water from the system to push the reaction equilibrium to the product side.

EXAMPLE 1

Fulleryne01 and Fulleryne02 (Scheme 3, Fisher Esterification). Fullerene alcohol (a1 or a2, 0.3 g, ~0.34 mmol), propiolic acid (0.565 g, 6.8 mmol), p-TsOH (29.3 mg, 0.17 mmol), 6 mL of 1-chloronaphthalene and 25 mL of toluene were added in a 100 mL round flask fitted with a Dean-Stark trap and a reflux condenser. Activated 4 Å molecular sieves were placed in the Dean-Stark trap, which was wrapped with cotton and aluminum foil to prevent heat loss. The mixture was stirred in an oil bath of 125° C. with steady reflux. After 24 h, the solution was cooled to room temperature and concentrated by rotary evaporator. The residual was directly applied to the top of the silica gel column. Hexane was first used to flush away the 1-chloronaphthalene. Toluene was then used as the eluent to afford the desired fullerynes as a black solid. Further elution with toluene/ethyl acetate mixed eluent (v/v=95/5) recovers the unreacted fullerene alcohol a1 or a2. For Fulleryne01, 98 mg was obtained with the yield of 34% and the recovery of the corresponding fullerene alcohol is 153 mg (51%). All of the characterizations were identical to the previous report. For Fulleryne02, 267 mg was obtained with the yield of 84% and the recovery of the corresponding

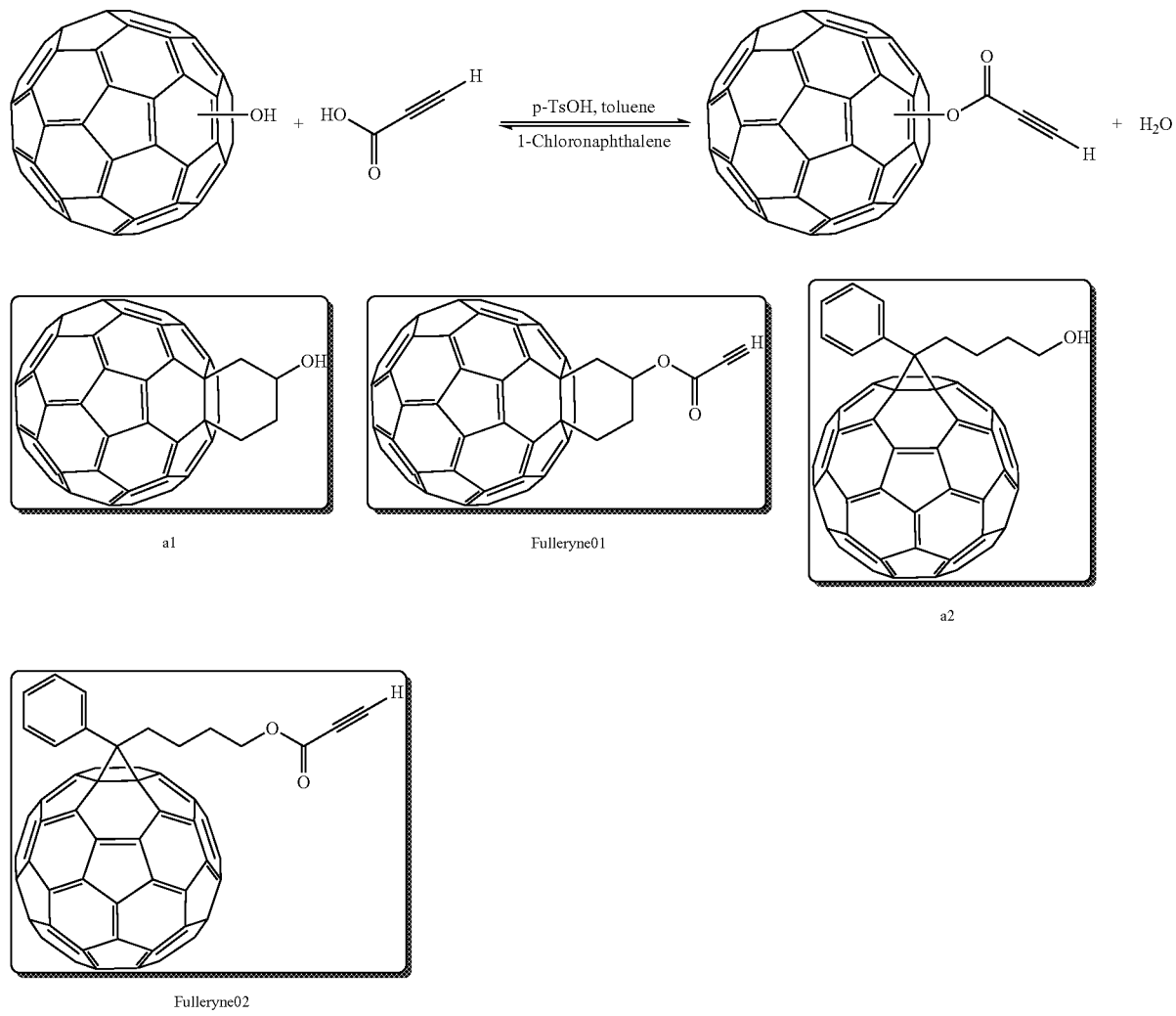

Scheme 3. Synthesis of Fulleryne01 and Fulleryne02 by Fischer Esterification fullerene alcohol is 15 mg (5%). The reaction using Soxhlet apparatus with activated 4 Å molecular sieves gave essentially the same results. To use the reactor shown in FIG. 1, the glassware was first completely dried by connecting to high vacuum line and flame-dried three times. Under argon, flask A was charged with fullerene alcohol a1 or a2 (0.50 g, ~0.63 mmol), p-TsOH (20 mg, 0.11 mmol), and 1-chloronaphthalene (16 mL) while flask B was charged with activated 4 Å molecular sieves. The whole system was further dried under vacuum for 4 h. Then, propiolic acid (1.0 mL, 1.138 g, 16.3 mmol) was added to flask A under argon and the system was degassed. Toluene (20 mL) was distilled into the reactor (flask A) by vacuum transfer. After purging with argon, both flask A and B were put into an oil bath of 125° C. to allow reflux and a continuous circulation of toluene going on from A to B to C and then back to A. After 24 h, the reactor was cooled down to room temperature and the materials in flask A were transferred out and concentrated under vacuum. The residue was directly applied to the top of silica gel for chromatography. The purification was then identical to that described previously for Fisher esterification using Dean-Stark or Soxhlet apparatus. The yield is 92% for Fulleryne01 and 93% for Fulleryne02. The reaction has been scaled up to 2.1 g of fullerene alcohols with slightly lower yield of 86%.

The second method relates to the production of fullerynes comprising reacting a ketone-functionalized fullerene (or named "fullerenone") with a variety of compounds including ethynyl Grignard agents; subsequently, quenching the addition product, the magnesium salt, by reaction with aqueous salts to form a fulleryne containing hydroxyl group, e.g., Fulleryne03, or subsequent reaction with functionalized acyl halides, such as bromoacetyl bromide or 6-bromohexanoyl bromide to form a fulleryne containing functional groups, such as bromine, connected via ester bond, for example, Fulleryne05 and Fulleryne06. The functional groups on fullerynes may undergo further transformation. For example, the hydroxyl-containing fulleryne, e.g. Fulleryne03, can be further reacted with a fluorinating agent such as bis(2-methoxyethyl)aminosulfur trifluoride, and form a fluorine-containing fulleryne, for example, Fulleryne04.

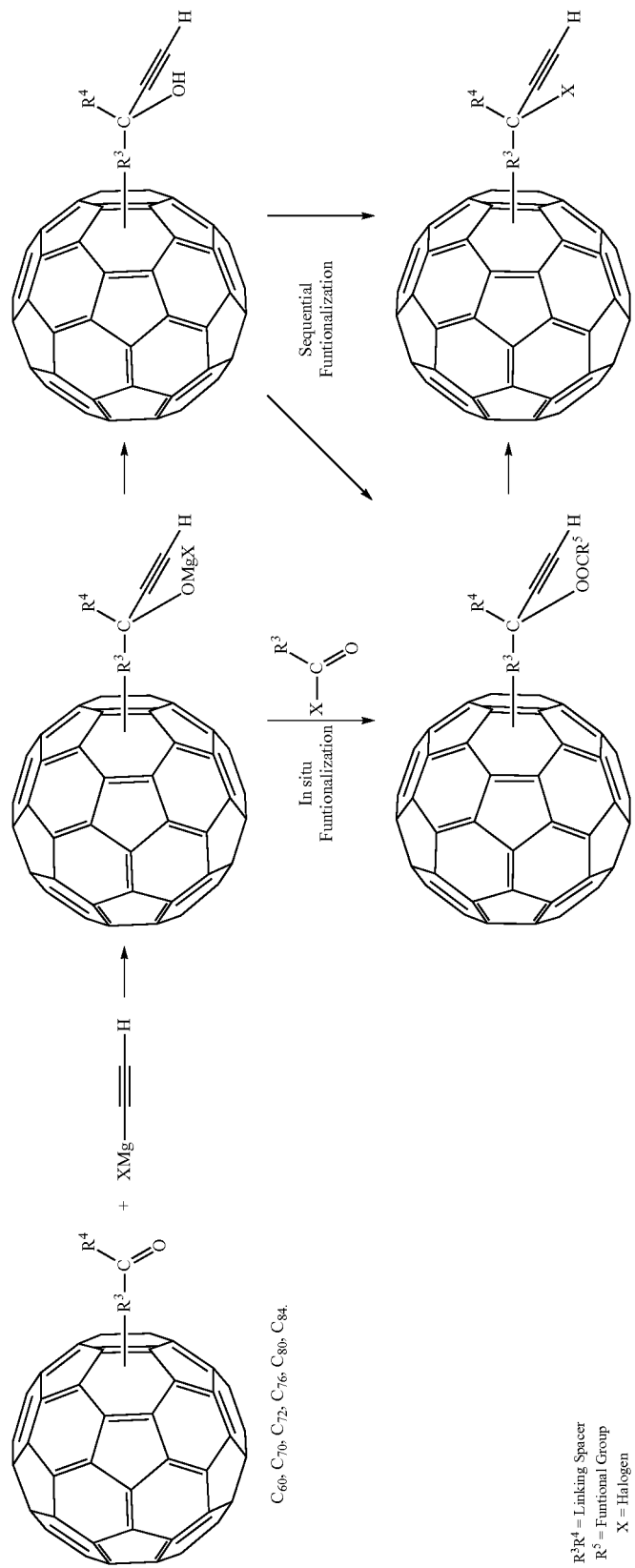

wherein $R^3$ can be a variety of spacers linking fullerene core as shown in Chart 4. $R^4$ is nonexistent or as set forth in Chart 4, and $R^5$ is as set forth in Chart 4. With respect to the production of Fulleryne03, 04, 05, and 06, the linking spacer is a formed 2-cyclohexyl ring fused to $C_{60}$, $C_{70}$, $C_{72}$, etc. core with $R^3$ being —($CH_2$—$CH_2$)— and $R^4$ being —($CH_2$)—. With respect to the production of Fulleryne04, X is fluoro. With respect to the production of Fulleryne05 and Fulleryne06, $R^5$ is —$(CH_2)_n$—Br where n is 1 or 5.

Chart 4. Various Linking Spacers Between $C_{60}$ and Carbonyl Group.

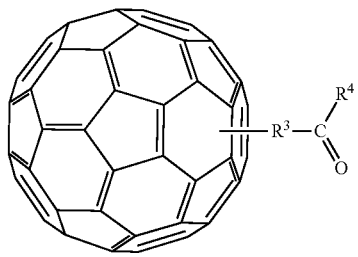

where —$R^3$— is —$CH_2CH_2^-$, —CH=CH—,

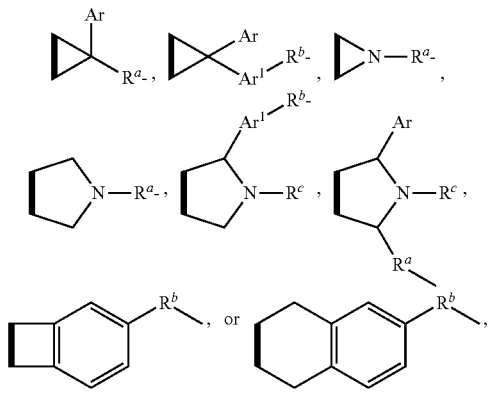

and
—$R^4$— is nonexistent, —$CH_2$—, or —$(CH_2)_n$H where n ranges from 0 to 8, or hydrogen, and
where $R^a$ is —$(CH_2)_n^-$,
$R^b$ is —$(CH_2)_n^-$ or —$O(CH_2)_n^-$,
$R^c$ is —$(CH_2)_n$H,
where n, independently for each $R^a$, $R^b$, and $R^c$, ranges from 1 to 8, Ar is

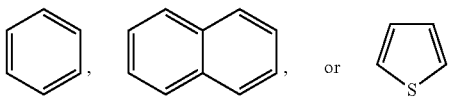

mono-substituted at different positions, and
$Ar^1$ is

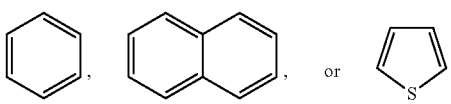

di-substituted as indicated;
where $R^5$ is —$(CH_2)_n$H, or —$(CH_2)_n$—X where n, independently, is from 1 to about 8,

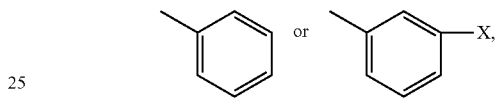

where X is fluoro, chloro, bromo, or iodo, or any combination thereof.

The second method utilizes a Grignard reagent such as 1-ethynylmagnesium chloride to add to carbonyl groups in fullerene derivatives (e.g., 2 in Scheme 1) which takes place exclusively and efficiently without reaction with the double bonds on $C_{60}$ core (Scheme 4). This is due to the reduced nucleophilicity and higher stability of 1-ethynylmagnesium chloride Grignard reagent. The sp hybridization of the carbon on the acetylene group increased its stability as an anion and tremendously reduced its nucleophilicity. The Grignard reactants preferably have an alkyne group but it can also have dialkyne and even trialkyne groups and also contain halogens such as fluoro, or chloro, or bromo, or iodo. No protection of the acetylene group was necessary. This is in contrast to the use of heretofore initial lithium organyls or other Grignard reagents that would add to $C_{60}$ with possible multi-additions in an uncontrollable manner. Another advantage is that the product, Fulleryne03, contains a hydroxyl group, which is very versatile in transforming into other functionalities via the sequential functionalization strategy for the preparation of multi-functional fullerynes. The intermediate, fullerenic magnesium salts, can be functionalized further in situ by quenching with acyl halides, such as bromoacetyl bromide, or other reactive agents, in a one-pot process.

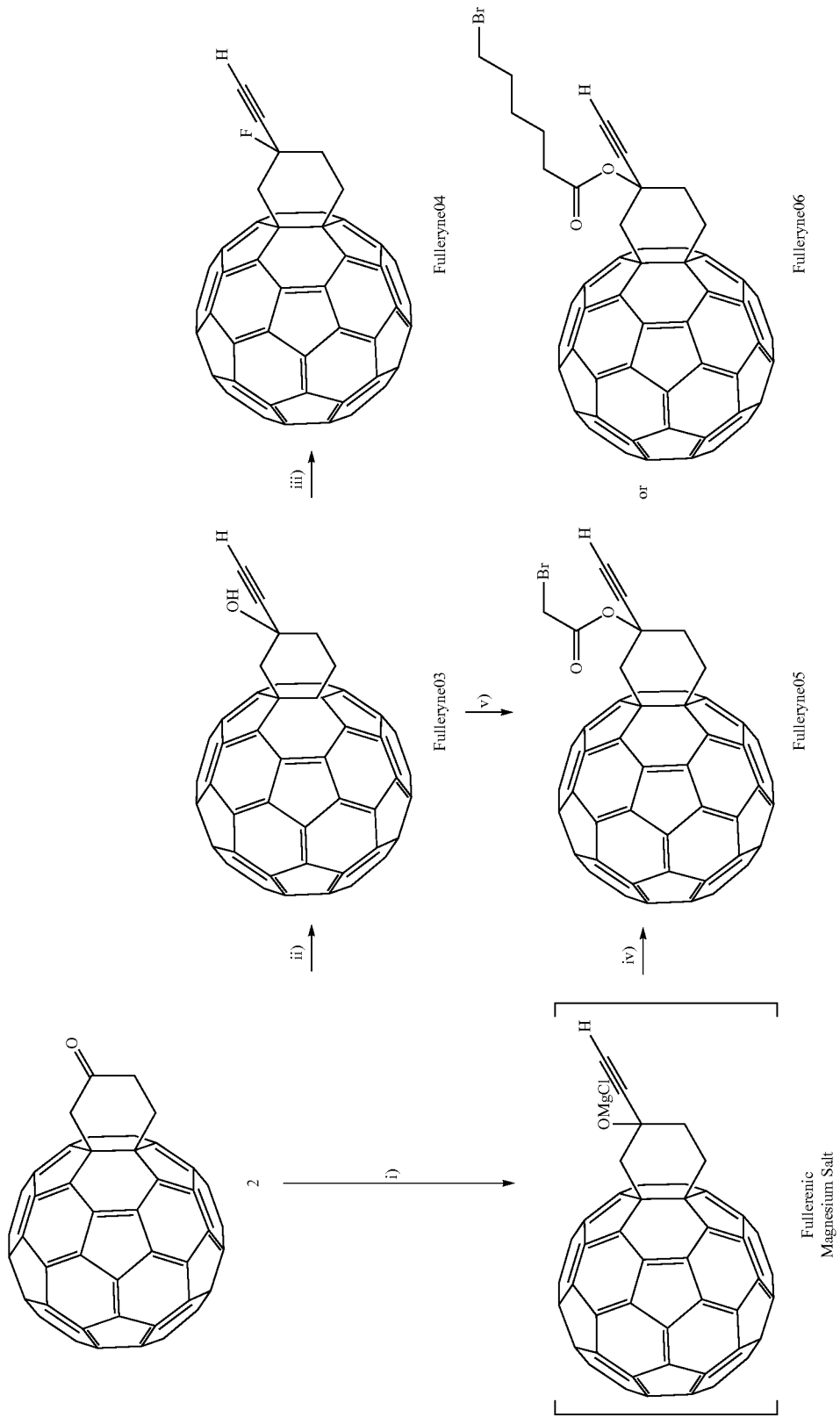

The method is also applicable to higher addition products in a similar approach to prepare multi-alkyne-functionalized fullerenes, namely, di-alkyne-functionalized fulleryne (fullerdiyne) and tri-alkyne-functionalized fulleryne (fullertriyne) (see Scheme 5 for the exemplary synthesis of fullerdiynes). It should be noted that the higher addition products were obtained as mixtures of regio-isomers in this case. Nevertheless, these multi-alkyne-functionalized fullerenes are useful intermediates in the synthesis of fullerene polymers or bucky gels. When necessary, regio-controlled addition products can also be obtained. Moreover, the method described is equally applicable to the synthesis of fullerynes from other fullerene derivatives bearing carbonyl groups.

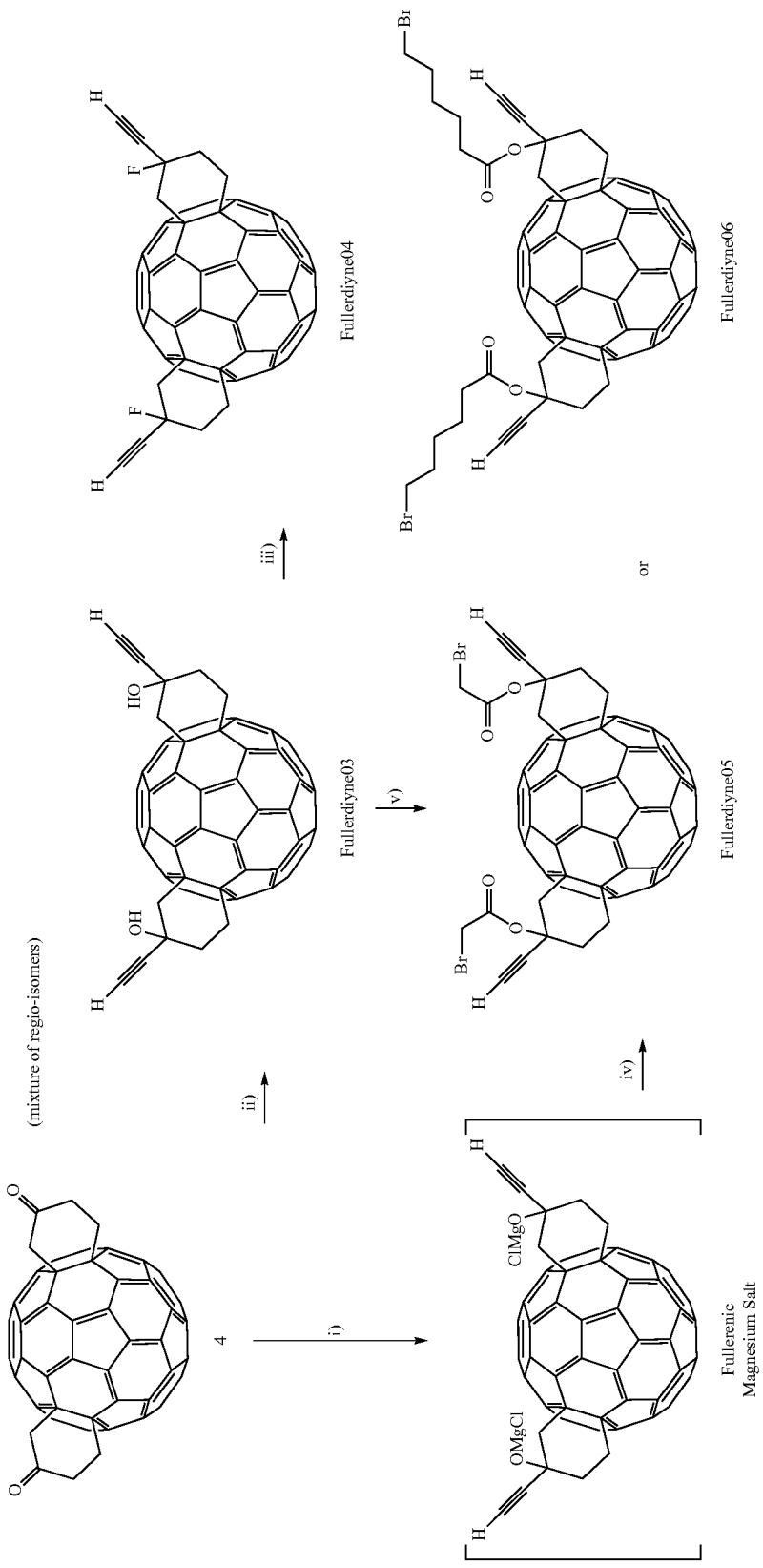

Scheme 6. The Addition of 1-Ethynylmagnesium Chloride to Carbonyl Groups as a Versatile Method in the Preparation of Fullerdiynes. Scheme 6 is the same as Scheme 4 except for the addition of two funtional groups instead of one.

a (i) 1-ethynylmagnesium chloride, toluene, r.t.; (ii) H₂O, r.t.; (iii) Deoxo-Fluor®, toluene, 0° C.; (iv) bromoacetyl bromide, toluene, r.t.; (v) bromoacetyl bromide (or bromohexanoyl bromide); toluene, r.t.; (v) bromoacetyl bromide (or bromohexanoyl bromide), NEt₃, 65° C..

Schemes 3, 4, 5, and 6 relate to the production of Fulleryne01, Fulleryne02, Fulleryne03, Fulleryne04, Fulleryne05 and Fulleryne06 utilizing the above-noted methods of the present invention. The advantages of utilizing such methods are supported by actual examples of the preparation of the noted fulleryne compounds.

ADVANTAGES OF THE PRESENT INVENTION

The methods and processes of the present invention have significant advantages as follows: (a) preparation of fullerynes is high yielding and easy to scale up; (b) "living" functionalization to install additional functionalities to fullerynes in a one-pot procedure; (c) general processes for preparation of fullerynes from hydroxyl-functionalized or carbonyl-functionalized fullerene derivatives; (d) multi-alkyne-functionalized fullerene (e.g. fullerdiynes and fullertriynes) can be synthesized in a similar manner.

For example, preparation of Fulleryne01 has high weight yields such as from about 65 to about 97%, desirably from about 70 to about 96%, and preferably from about 80 to about 95%. The preparation of Fulleryne02 also has high weight yields such as from about 82 to about 92%, desirably from about 85 to about 90%. When the solvent (1-chloronaphthalene) and the common Dean-Stark apparatus are used, satisfactory yields around 85% can be obtained. When the specially designed reactor is used, the yield can be further improved to about 90%. Both results are high in comparison with prior art yields of only trace amount using Fischer reaction in toluene or of only about 17% using Steglich reaction. The reaction temperatures for the preparation of Fulleryne01 and Fulleryne02 are generally from about 110° C. to about 135° C. where a reflux is conveniently maintained, and preferably from about 115° C. to about 130° C., with about 120° C. to about 128° C. being preferred. The alkyne-containing acid should be used in excess. The ratio between alkyne-containing acid and fullerene alcohol for Fulleryne01 and Fulleryne02 should be from about 5:1 to about 50:1, desirably from about 10:1 to about 30:1, and preferably from about 15:1 to about 25:1. The choice of Lewis acid catalyst can be varied, such as p-toluenesulfoinic acid (p-TsOH), sulfuric acid, hydrochloric acid, etc., or other Lewis acids, such as various boron trihalides, or various organoboranes, or any combination thereof. The ratio of the acid catalyst to fullerene alcohol is from about 0.1 to about 100%, desirably from about 0.5 to about 10%, and preferably from about 1 to about 5% by mole. The solvent must have high solubility and high boiling point while inert to the reaction system. An aromatic hydrocarbon solvent, such as 1-chloronaphthalene, 1-methylnaphthalene, or 1,2-dichlorobenzene, is usually preferred. Other solvents capable of azeotropically removing water from system, such as toluene or benzene, should be used in combination. Aliphatic solvents such as hexane, heptane, and the like are avoided, or if utilized, the amount thereof is very low, such as about 10% by weight or less, desirably about 5% by weight or less, preferably from about 2% or about 1% by weight based upon the total weight of the solvent system and most preferably nil, that is no aliphatic solvent. The amount of solvent to be used is preferably the minimum to dissolve the fullerene compounds. The compound used to remove the water should be inert to the reaction conditions. Molecular sieves are most preferable. Other drying reagents include but are not limited to $CaH_2$, NaH, $P_2O_5$, etc.

Fulleryne03 in Scheme 5 has high weight yields such as from about 80% to about 97%, desirably from about 84% to about 96%, and preferably from about 88% to about 95%. The weight yield of Fulleryne04 is also fairly high and is from about 60% to about 85% with from about 70 to about 80% being preferred. The weight yield with regard to the preparation of Fulleryne05 and Fulleryne06 are generally the same and range from about 40% to about 80% and preferably from about 60% to about 75%. With respect to Scheme 6, generally the chemistry is the same except that difunctional groups exist in fullerene. The reaction temperatures for forming Fulleryne03 are generally from about −30° C. to about 30° C., and preferably from about 15° C. to about 30° C., with about 20° C. to about 28° C. being preferred. The reaction temperature for forming Fulleryne04 is generally low from, for example, about minus 30° C. to about 30° C., and desirably from about minus 20° C. to about +10° C. with about minus 0.5° C. to about +5° C. being preferred. The preparation of Fulleryne05 and Fulleryne06 utilizing an acyl halide, with the acyl group having from about 1 to about 8 carbon atoms and the halide being fluoro, chloro, bromo, or iodo, by in situ functionalization is generally at temperatures from about 0° C. to about +25° C., desirably from about 0° C. to about 15° C., and preferably about 2° C. to about 10° C. The preparation of Fulleryne05 and Fulleryne06 utilizing an acyl halide by sequential functionalization from Fulleryne03 is also generally at temperatures from about 0° C. to about 100° C., desirably from about 25° C. to about 80° C., and preferably about 55° C. to about 75° C. With regard to the preparation of the Fullerdiynes set forth in Scheme 6, the temperature preparation is generally the same as with respect to Scheme 5 and is hereby fully incorporated by reference. The equivalent ratio of 1-ethynylmagnesium halide to fullerenone (carbonyl-containing fullerene) for the preparation of Fulleryne03, 04, 05, and 06 should be from about 1 to about 3, desirably from about 1.05 to about 1.5, and preferably from about 1.1 to about 1.3. The solvent should solubilize the fullerenone. Aromatic solvents are desired and preferred solvents include benzene, toluene, chlorobenzene, bromobenzene, and o-dichlorobenzene. Generally, aliphatic solvents are not utilized since the solubility of the various fullerene derivatives therein are poor. The stoichiometry of various quenching agents, such as water, methanol, to convert the fullerenic magnesium salt to Fulleryne03 is utilized in excess, typically from 1 equivalent to 1000 equivalents and desirably from 2 equivalents to 100 equivalents. The ratio of the functionalizing agents, such as acyl halide to the fullerenic magnesium salt to prepare Fulleryne05, and 06, is generally used in excess, typically from about 2 equivalent to about 100 equivalents, desirably from about 2 equivalents to about 20 equivalents, and preferably about 3 to about 10 equivalents. The ratio of Deoxo-Fluor® (bis(2-methoxyethyl)aminosulfur trifluoride) reagent to Fulleryne03 in the preparation of Fulleryne04 is generally from about 1.05 to about 2, and desirably from about 1.05 to about 1.5 with from about 1.06 to about 1.3 equivalents being preferred. With regard to the preparation of the Fullerdiynes set forth in Scheme 6, the stoichiometry in preparation is generally twice as with respect to Scheme 4 and is hereby fully incorporated by reference.

In comparison with the prior art, previously, the Steglich reaction in the synthesis of Fulleryne01 only gave 17% yield and the yield was too low to be applied to the preparation of fullerdiynes and fullertriynes. Other methods, such as Bingle-Hirsch reaction to introduce alkyne group into fullerene requires careful control on stoichiometry and reaction conditions to avoid side reactions associated with the halogenation of hydrogen at the alkyne, or a protection-deprotection scheme is required. The present method requires no protection of the alkyne group. The reduced nucleophilicity and higher stability of this Grignard reagent, 1-ethynylmagnesium chloride, makes it unreactive towards the double bonds on $C_{60}$ core but remains highly active towards carbonyl groups. An important aspect of the present invention is that addition takes place quantitatively. Using different quenching reagents, one-pot functionalization of the magnesium salt intermediate is possible and high yielding, which allows a facile procedure for the preparation of multifunctional fullerynes. This reaction is quite versatile in that it can react with any carbonyl groups present in the fullerene derivative without side reactions with the central $C_{60}$ core. Fullerdiynes are also possible from diaddition to 4 using a similar process. The fullerdiynes are useful intermediates in the synthesis of fullerene polymers or fullerene gels.

The following examples serve to illustrate, but not to limit the present invention.

EXAMPLE 2

Fulleryne03 (Scheme 5). To a degassed solution of 2 (100 mg, 0.126 mmol) in 100 mL of toluene, a 1-ethynylmagnesium.chloride solution in THF (0.5 mL, 0.25 mmol) was added dropwise via syringe at 25° C. The clear dark brown solution immediately turned turbid. After 30 minutes, 1 mL of saturated aqueous ammonium chloride solution was added to quench the reaction. The solution turned clear and dark brown again with stirring. The solution was then washed with water twice and dried over anhydrous $Na_2SO_4$. After removal of the solvent, the product was purified chromatographically on silica gel (toluene, $R_f$=0.35) to give Fulleryne03, as a brown solid (94 mg, 92%). $^1$H NMR ($CS_2$:$CDCl_3$=1:2, 500 MHz, ppm, δ): (see also figure 6.6) 4.00 (m, 1H), 3.85 (m, 1H), 3.50 (m, 3H), 3.19 (m, 1H), 2.82 (s, 1H), 2.58 (s, 1H).

$^{13}$C NMR ($CS_2$:$CDCl_3$=2:1, 125 MHz, ppm, δ): 29.83, 34.76, 38.94, 50.22 (C—OH), 61.30 ($C_{60}$, sp$^3$-C), 63.56 ($C_{60}$, sp$^3$-C), 73.06 (C≡CH), 88.58 (C≡CH), 135.22, 141.37, 141.84, 142.36, 145.19, 145.23, 146.00, 146.22, 147.43, 155.76, 156.06, 156.91. FT-IR (KBr) v (cm$^{-1}$): 3300 (≡C—H), 527 (C—C in $C_{60}$). MS (MALDI-TOF): Calcd for $C_{66}H_8O$ 816.06. Found: 816.18 (100%) (M$^+$).

EXAMPLE 3

Fulleryne04 (Scheme 5). To a degassed solution of Fulleryne03 (158 mg, 0.194 mmol) in 100 mL of toluene cooled to 0° C. was added dropwise bis(2-methoxyethyl)aminosulfur trifluoride (88 mg, 0.40 mmol) via syringe. After 1 h, TLC showed that the reaction was complete and it was then quenched by the addition of 5% aqueous $NaHCO_3$ solution. The solution was then washed with water twice and dried over anhydrous $Na_2SO_4$. After removal of the solvent, the product was purified chromatographically on silica gel (cyclohexane:toluene=1:1 volume ratio, $R_f$=0.8) to give Fulleryne04, as a brown solid (120 mg, 76%). FT-IR (KBr) v (cm$^{-1}$):3300 (≡C—H), 527 (C—C in $C_{60}$). MS (MALDI-TOF): Calcd for $C_{66}H_7F$ 818.05. Found: 818.05 (100%)(M$^+$)

EXAMPLE 4

Fulleryne05 (Scheme 5). To a degassed solution of 2 (100 mg, 0.126 mmol) in 100 mL of toluene, an ethynylmagnesium chloride solution in THF (0.5 mL, 0.25 mmol) was added dropwise via syringe at 25° C. The clear dark brown solution immediately turned turbid. After 30 minutes, bromoacetyl bromide (0.58 g, 0.25 mL, 2.87 mmol) was added to quench the reaction. The solution gradually turned clear and then dark brown again after overnight stirring. The solution was then washed with water twice and dried over anhydrous $Na_2SO_4$. After removal of the solvent, the product was purified chromatographically on silica gel (cyclohexane:toluene=1:1 volume ratio, $R_f$=0.7) to give Fulleryne05, as a brown solid (81 mg, 68%). Further eluting with toluene yielded Fulleryne03 (21 mg, 19%). $^1$H NMR ($CS_2$:$CDCl_3$=1:2, 500 MHz, ppm, δ): 4.30 (d, 1H), 4.11 (d, 1H), 3.92 (s, 2H), 3.65 (m, 2H), 3.45 (m, 2H), 2.95 (s, 1H). $^{13}$C NMR ($CS_2$:$CDCl_3$=2:1, 125 MHz, ppm, δ): 26.04, 29.82, 34.40, 36.89, 47.07 (C—O), 60.92 ($C_{60}$, sp$^3$-C), 63.39 ($C_{60}$, Sp$^3$-C), 75.57 (C≡CH), 83.68 (C≡CH), 134.95, 135.67, 141.49, 141.55, 142.45, 145.34, 145.37, 145.63, 146.28, 155.05, 155.38, 155.48, 156.17, 164.74 (C=O). FT-IR (KBr) v (cm$^{-1}$): 3294 (≡C—H), 1745 (C=O), 527 (C—C in $C_{60}$). MS (MALDI-TOF): Calcd for $C_{68}H_9BrO_2$ 935.98. Found: 935.99 (100%) (M$^+$).

EXAMPLE 5

Fulleryne06 (Scheme 5). To a degassed solution of 2 (100 mg, 0.126 mmol) in 100 mL of toluene, a 1-ethynylmagnesium chloride solution in THF (0.5 mL, 0.25 mmol) was added dropwise via syringe at 25° C. The mixture was stirred at room temperature for 15 min before 0.2 mL dry acetone was added to quench the excess Grignard reagent. Then 6-bromohexanoyl chloride (0.1 mL, 0.63 mmol) was added via a syringe. The mixture was further stirred at room temperature overnight before quenched by the addition of saturated sodium bicarbonate aqueous solution. The organic phase was separated and washed with water and brine, dried over $MgSO_4$ and concentrated under vacuum. The residue was purified by silica gel column chromatography with pure toluene as the eluent to afford the product as a black powder (71 mg, 57%). $^1$H NMR ($CDCl_3$, 300 MHz, ppm): δ 4.23 (1H, d, J=15 Hz), 4.06 (1H, d, J=15 Hz), 3.66 (2H, m), 3.38 (4H, m), 2.92 (1H, s), 2.44 (2H, m), 1.88 (2H, m), 1.71 (2H, m), 1.55 (2H, m). MS (MALDI-TOF, m/z): calc. 992.0. found 992.1 (M$^+$).

Generally, hydrocarbon solvents can be utilized, whether aliphatic or preferably aromatic, and specific examples include petrolene ether, benzene, toluene, hexane, heptane, xylene, mestylene, or halogenated such as chlorobenzene, bromobenzene, o-dichlorobenzene, 1-chloronaphthalene, and the like. The amount of solvent is generally in effective amounts such that the reactants are dissolved therein.

The Cu(I)-catalyzed [3+2] cycloaddition reaction between alkyne and azides (CuAAC) are known to be a typical "click" chemistry exhibiting high reactivity and high efficiency. When this is applied to the synthesis of fullerene materials, the alkyne group is usually installed on the fullerene. The alkyne-functionalized fullerene is thus named "fulleryne". The reaction between fulleryne and azide-functionalized materials has been demonstrated by many studies to be an effective way to introduce fullerene into functional materials, ranging from small molecules, star molecules, dendrimers, viral nanoparticles, to polymers and surfaces. The method is very versatile for preparing fullerene hybrid materials and could be viewed as a general functionalization scheme for introducing fullerene into a functional material. However, its practical application was hindered by the availability of fullerynes. For example, the 17% yield in the Steglich esterification was a bottle-neck in the overall process using Fulleryne01 to synthesize fullerene polymers (Scheme 1). From the mechanism, it is recognized that if an electron-withdrawing group is adjacent to alkyne, it will promote the reactivity of alkyne towards cycloaddition. For example, 1-ethynylcyclohexanol derivatives that are known to possess high reactivity towards CuAAC reaction due to the σ-electron-withdrawing group adjacent to the alkyne.

Accordingly, the various fullerynes of the present invention including the above-noted specific Fullerynes01 through 06 can be reacted via standard click chemical reaction such as azide alkyne Huisgen cycloadditon utilizing copper catalysts generally at room temperature. For example, click reactions have been carried between fullerynes of the present invention and PS—$N_3$ whereby fullerene-end capped polymers were exclusively obtained with over 90% yield. Thus, a variety of functional groups can be added to the fulleryne compounds of the present invention including, but not limited to fluorescent groups, liquid crystal mesogens, dendrimers, perfluorinated alkyl chains, polyhedral oligomeric silsesquioxanes, ferrocenes, bio-active molecules, proteins, and the like. The general scheme for such reactions is set forth in Scheme 7 wherein the "R" group on the fulleryne represents the compounds or groups added to the Fulleryne according to the present invention, for example embodiments of Fullerynes02 through 06, and "F" represents the functional materials noted immediately above.

Scheme 7. General Funtionalization of Fulleryne via "Click" Chemestry

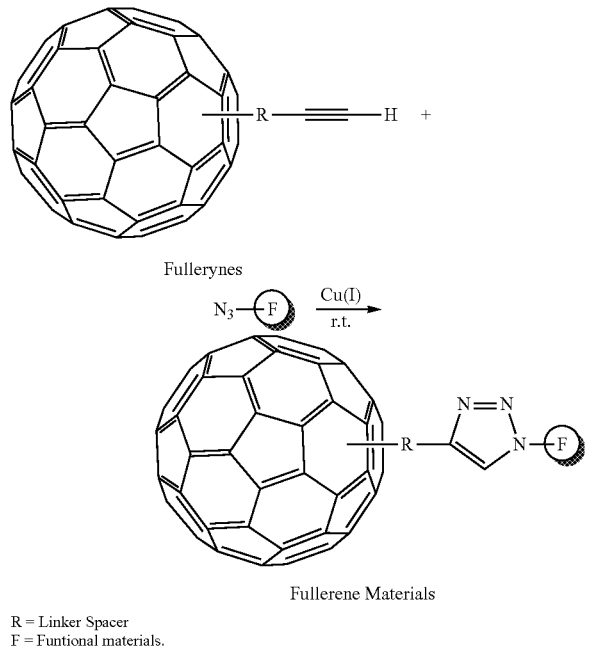

R = Linker Spacer
F = Funtional materials.

The "click" chemistry approach to incorporate fullerene into functional materials is particularly useful when the materials to be functionalized are unstable under more drastic reaction conditions (e.g., biological molecules), or when the products are very difficult to separate (e.g., polymers), or when the materials are heterogeneous (e.g., surfaces, nanoparticles, etc.). The ready availability of highly reactive and multifunctional fullerynes can result in the preparation of numerous types of fullerene compounds. The prototype Fulleryne01 was shown to be very reactive and "clicked" to azide-functionalized polymers (such as PS—$N_3$) in high efficiency to yield a well-defined structure with 100% fullerene functionality. In this way, no complicated purification procedures, such as fractionation, were necessary.

The fullerynes described in the present invention have the following applications: (1) they can be used directly or as a component for a variety of applications, including organic photovoltaics, polymer electronics, antioxidants, biopharmaceuticals, phototherapeutic agents, addictives, catalysts, and MRI agents, etc.; (2) they can be used as an intermediate for the synthesis of fullerene hybrid materials, such as fullerene polymers, fullerene hydrogels, and fullerene bio-conjugates, useful for a variety of applications including organic photovoltaics, polymer electronics, antioxidants, biopharmaceuticals, phototherapeutic agents, addictives, catalysts, and MRI agents, etc.

While in accordance with the patent statutes the best mode and preferred embodiment have been set forth, the scope of the invention is not intended to be limited thereto, but only by the scope of the attached claims.

What is claimed is:
1. A functionalized fulleryne composition, comprising: the formula

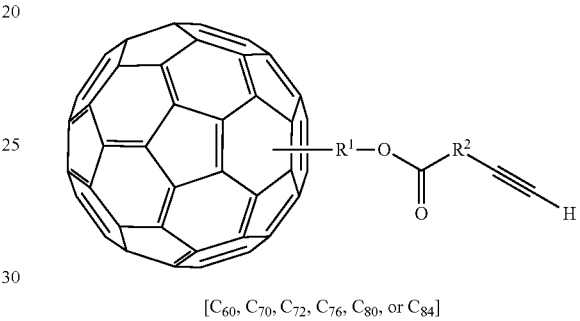

[$C_{60}$, $C_{70}$, $C_{72}$, $C_{76}$, $C_{80}$, or $C_{84}$]

where —$R^1$— is

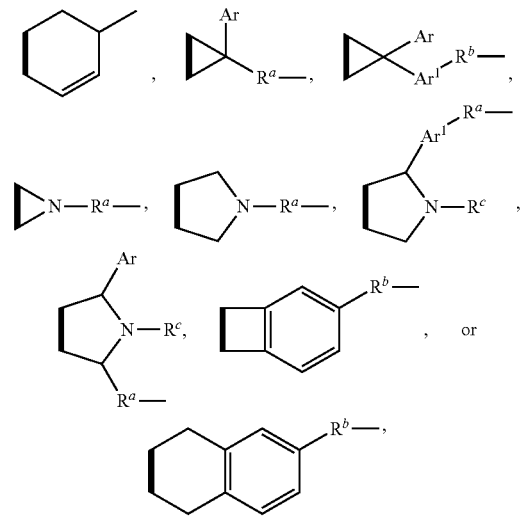

and where $R^a$ is —$(CH_2)_n$—, $R^b$ is —$(CH_2)_n$— or —$O(CH_2)_n$—, $R^c$ is —$(CH_2)_n H$, where n, independently for each $R^a$, $R^b$, and $R^c$, ranges from 1 to 8, Ar is

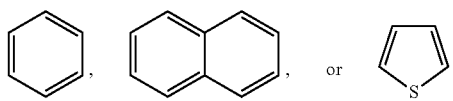

mono-substituted at different positions, and Ar¹ is

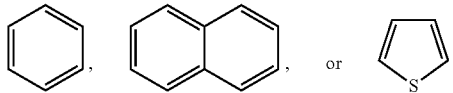

di-substituted as indicated, and wherein R² is nonexistent or is an alkyl having from 1 to about 6 methylene units; or wherein said $C_{60}$, $C_{70}$, $C_{72}$, $C_{76}$, $C_{80}$, or $C_{84}$ has an additional

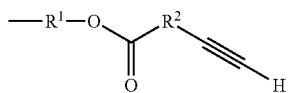

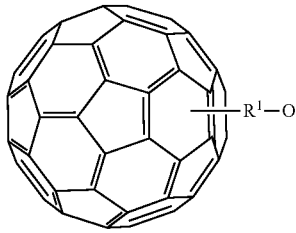

[$C_{60}$, $C_{70}$, $C_{72}$, $C_{76}$, $C_{80}$ or $C_{84}$]

group wherein R¹ and R², independently are the same or different as the above R¹ and R² groups.

2. The functionalized fulleryne composition of claim 1, wherein said fulleryne has 60 or 70 carbon atoms.

3. The functionalized fulleryne composition of claim 2, wherein said R¹ is

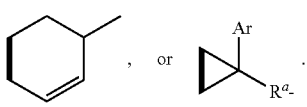

4. The functionalized fulleryne composition of claim 3, wherein R¹ is

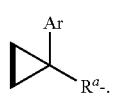

5. The functionalized fulleryne composition of claim 3, wherein R² is nonexistent or from about 1 to about 3 methylene units.

6. The functionalized fulleryne composition of claim 1, wherein said fulleryne has the formula

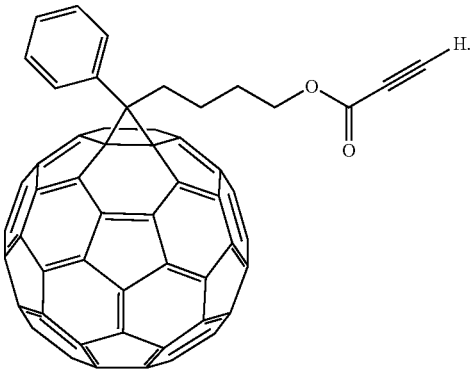

[$C_{60}$, $C_{70}$, $C_{72}$, $C_{76}$, $C_{80}$, or $C_{84}$]

7. A method for preparing a fulleryne by an esterification reaction comprising the steps of: reacting

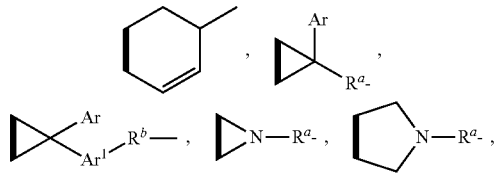

where —R¹— is

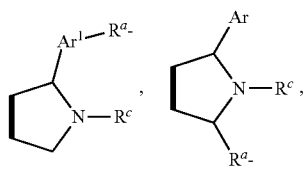

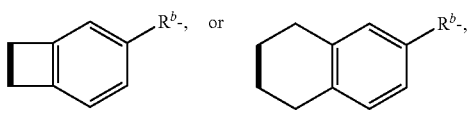

and where $R^a$ is, —$(CH_2)_n$—, $R^b$ is —$(CH_2)_n$—or, —$O(CH_2)_n$—, $R^c$ is —$(CH_2)_n H$, where n, independently for each $R^a$, $R^b$, and $R^c$, ranges from 1 to 8, Ar is

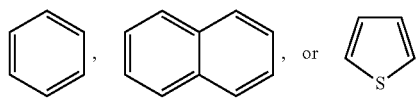

mono-substituted at different positions, and Ar¹ is

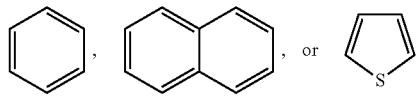

di-substituted as indicated, and wherein $R^2$ is nonexistent or is an alkyl having from 1 to 6 methylene units; and wherein said

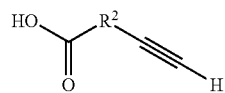

in equivalent excess with respect to said

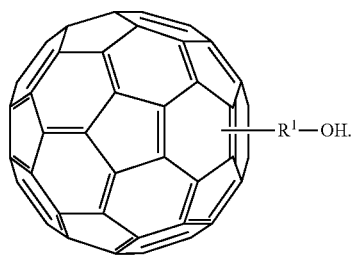

[$C_{60}$, $C_{70}$, $C_{72}$, $C_{76}$, $C_{80}$, or $C_{84}$]

8. The process of claim 7, wherein said excess of said acid compound to said fullerenol compound is from about 5:1 to about 50:1, and wherein said step of reacting takes place in the presence of a Lewis acid catalyst.

9. The process of claim 8, wherein said excess acid to fullerenol equivalent ratio is from about 10:1 to about 30:1, and said reaction is carried out at a temperature of from about 110° C. to about 135° C.

10. The process of claim 9, wherein said step of reacting takes place in an aromatic solvent, wherein said reaction temperature is from about 115° C. to about 130° C., and wherein said Lewis acid catalyst is p-toluenesulfoninic acid (p-TsOH), sulfuric acid, hydrochloric acid, a boron trihalide, or an organoborane, or any combination thereof.

\* \* \* \* \*